United States Patent
Uihlein (10) Patent No.: US 8,852,203 B2
(45) Date of Patent: Oct. 7, 2014

(54) MULTI-WIRE INSTRUMENT, IN PARTICULAR FOR ENDOSCOPES

(75) Inventor: Bernhard Uihlein, Dettingen (DE)

(73) Assignee: EPflex Feinwerktechnik GmbH, Dettingen/Ems (DE)

(*) Notice: Subject to any disclaimer, the term of this patent is extended or adjusted under 35 U.S.C. 154(b) by 1553 days.

(21) Appl. No.: 12/160,585

(22) PCT Filed: Jan. 11, 2007

(86) PCT No.: PCT/EP2007/000203
§ 371 (c)(1), (2), (4) Date: Jul. 10, 2008

(87) PCT Pub. No.: WO2007/082671
PCT Pub. Date: Jul. 26, 2007

(65) Prior Publication Data
US 2010/0168758 A1 Jul. 1, 2010

(30) Foreign Application Priority Data
Jan. 11, 2006 (DE) .......... 10 2006 002 531

(51) Int. Cl.
*A61B 17/24* (2006.01)
*A61B 17/00* (2006.01)
*A61B 17/221* (2006.01)
*A61B 19/00* (2006.01)

(52) U.S. Cl.
CPC ... *A61B 17/00234* (2013.01); *A61B 2017/2212* (2013.01); *A61B 17/221* (2013.01); *A61B 2019/307* (2013.01)
USPC ............................ 606/113; 606/114; 606/127

(58) Field of Classification Search
USPC .................. 606/127, 113, 159, 200, 114, 110
See application file for complete search history.

(56) References Cited

U.S. PATENT DOCUMENTS 4,046,150 A * 9/1977 Schwartz et al. ............. 606/127
6,013,086 A 1/2000 Ouchi et al.
(Continued)

FOREIGN PATENT DOCUMENTS

DE 86 04 065.0 U1 7/1986
DE 89 04 213.1 U1 7/1989
(Continued)

OTHER PUBLICATIONS

Nayler, G.H.F. Dictionary of Mechanical Engineering. 3rd ed. Boston: Butterworths, 1985. 365. Print.*
(Continued)

Primary Examiner — Tuan V Nguyen
Assistant Examiner — Tin Nguyen
(74) Attorney, Agent, or Firm — Crowell & Moring LLP (57) ABSTRACT

A multi-wire instrument has a distal functional section, in which a plurality of individual wires form a wire basket, wherein they are combined at a distal end and connected to one another by being joined directly to one another or to a distal terminating body while forming a respective predetermined breaking connection. A shaft section extends between the distal functional section and a proximal end region of the multi-wire instrument. The individual wires extend in one piece from their distal end to the proximal end region of the multi-wire instrument and the shaft section is formed by the individual wires, which are combined there and held together. The individual wires are twisted together in the entire shaft section up to the basket-forming functional section, wherein they merge from the twisted distal end of the shaft section with radial widening, and/or the individual wires are twisted together in a distal end region which adjoins the basket-forming functional section in a distal manner and in this case abut one another along this twisting.

17 Claims, 5 Drawing Sheets

(56) References Cited

U.S. PATENT DOCUMENTS

| | | | |
|---|---|---|---|
| 6,187,017 | B1 | 2/2001 | Gregory, Jr. |
| 6,299,612 | B1 * | 10/2001 | Ouchi .............................. 606/47 |
| 6,319,261 | B1 | 11/2001 | Bowers |
| 2002/0091394 | A1 | 7/2002 | Reynolds et al. |

FOREIGN PATENT DOCUMENTS

| | | |
|---|---|---|
| DE | 295 06 568 U1 | 7/1996 |
| DE | 197 22 429 A1 | 12/1998 |
| DE | 199 41 912 A1 | 4/2000 |
| DE | 201 07 567 U1 | 10/2002 |
| DE | 10 2005 030 010 A1 | 1/2006 |
| DE | 10 2004 055 375 A1 | 6/2006 |
| FR | 2 317 903 A1 | 2/1977 |

OTHER PUBLICATIONS

Forms PCT/IB/338 & 373 and PCT/ISA/237 (eight (8) pages).
International Search Report dated May 22, 2007 including English translation (Six (6) pages).
German Office Action dated Oct. 25, 2006 including English translation of the relevant portion (Nine (9) pages).

* cited by examiner

Fig. 11  Fig. 12  Fig. 13

MULTI-WIRE INSTRUMENT, IN PARTICULAR FOR ENDOSCOPES

BACKGROUND AND SUMMARY OF THE INVENTION

The invention relates to a multi-wire instrument, in particular, for endoscopes.

Various multi-wire instruments are used, particularly for endoscopes for example, in applications as calculus collecting basket instruments for collecting gall or kidney stones. In their functional condition in the distal functional section, the individual wires form a functional wire mesh in the shape of a small wire basket. The wire basket may also have the function of a snarl or filter unit. Typically, the distal functional section can be pulled into a guiding tube while the functional wire mesh is folded together and can be moved out of the guiding tube again while the functional wire mesh is unfolded. For this purpose, a superelastic material, such as an NiTi alloy, such as nitinol, can be preferably used for the individual wires.

In the case of a current instrument type, the individual wires are proximally guided together behind their distal functional section and are fixed on a proximally continuing shaft wire made of tube or strand material which forms the shaft section of the instrument; see U.S. Pat. No. 6,013,086. When the connection between the proximal ends of the function-forming distal individual wires and the distal end of the shaft wire tears unintentionally, for example, as a result of a tensile load when collecting a calculus, the use of this type of instrument may lead to difficulties.

As a remedy, German Published Patent Application DE 197 22 429 A1 suggests forming the individual wires of the distal functional section by an axial slotting of a solid or tube-shaped unworked wire in regions, which unworked wire acts as a shaft-side tension strand in the unslotted proximal region. While leaving a distal end stub, the axial slotting ends at a distance in front of the distal frontal end of the wire blank on which a, for example, spherical or hemispherical end element may be mounted.

The later Published German Patent Application DE 10 2004 055 375 A1 also describes a multi-wire unit which is made in one piece from a tube piece and has several wire pieces into which the tube piece is divided by way of axial slotting in regions, wherein, while leaving a distal wire connection region, the axial slots end at an appropriately small axial distance. As a result, in the functional condition of the multi-wire unit, the wire pieces form a, for example, small-basket-shaped functional wire mesh and the distal wire connection region is deformed into an essentially tipless forward end.

The later Published German Patent Application DE 10 2005 030 010 A1 describes a calculus collecting basket unit, wherein the basket region is formed by wire pieces, which are guided together at their distal end and are fixed to a distal head piece having a preset breaking point. This has the purpose of achieving that, in the event of an overload when in use, the head piece releases the wire pieces at their distal end, so that an undesirable uncontrolled tearing of other connection points can be avoided and/or a collected calculus can be released again.

The Registered Utility Model document DE 89 04 213 U1 discloses a multi-wire instrument of the above-mentioned type in the form of a lithotripter having a small collecting basket, which is formed of several collecting strands consisting of a wire material and extending in a bent manner toward the outside. The collecting strands converge at the tip of the collecting basket and are connected with a tension strand of several tension wires. The tension strand consists of a twice-twisted wire rope whose litz number corresponds at least to the number of collecting strands of the collecting basket, which are formed by deformed strands of the wire rope, extending from the wire rope to the tip of the collecting basket and being mutually fastened there with their free ends. At a proximal foot region of the collecting basket, the strands of the wire rope are held together by a sleeve in which the possibly existing other strands extending only in the shaft section also distally end. In a portion of the shaft section proximally adjoining the foot section of the collecting basket, the strands are untwisted from one another and extend in an untwisted manner, whereby the tension strand flexibility is to be increased. The strands forming the collecting basket extend in the same manner untwisted in their collecting basket section and in their adjoining distal end region, in which case they are fixed to one another with their free distal ends by way of soldering or clamping while forming a type of predetermined breaking point.

U.S. Pat. No. 6,187,017 B1 discloses a calculus collecting basket instrument having a specific collecting basket design, in which two pair-generating individual wires respectively adjoining the basket-forming section in the distal direction first cross one another while forming a first crossing point, then radially move away from one another again and, subsequently, while forming a second crossing point, are guided together again while crossing one another in order to then, in a purely axial direction, be fixed in an abutting manner to an atraumatic cylindrical terminating body. In this case, at both crossing points, one wire may both times be disposed under or over the other wire or once may be situated over and the other time may be situated under the other wire. The individual wires are fixed with their proximal end directly behind their basket-forming section on a separate shaft body.

Especially for medical applications, for example, for nephrolithotomies, a cross-section or diameter is desirable for the multi-wire instrument that is as small as possible in order to be able to introduce the latter into corresponding tissue canals without any problems. Simultaneously, the functional wire mesh provided by the individual wires has to guarantee the properties required for its function, particularly with respect to stability or strength and flexibility or rigidity.

The invention is based on the technical problem of providing a multi-wire instrument of the above-mentioned type which can be implemented at relatively low expenditures and, as required, with a comparatively small cross-section or diameter also in its shaft section, and in the case of which the danger is minimized that connection points tear in an undesired manner when the instrument is in use.

According to the invention, a multi-wire instrument is provided in which individual wires are joined at the distal end by way of a respective predetermined breaking connection directly to one another or to a distal terminating body and extend in one piece from the distal end to the proximal end region of the multi-wire instrument, the shaft section being formed by the individual wires combined there and held together.

Since the individual wires are implemented in one piece from the distal end to the proximal end region of the multi-wire instrument, there is no additional shaft wire to which the individual wires have to be fixed and, therefore, no connection point of the proximal ends of the individual wires with the distal end of a proximally adjoining shaft section. On the contrary, the individual wires themselves form the entire shaft section in the corresponding region. This eliminates the risk that such connection points undesirably tear during use when stressed. Rather, as a result of the fact that the predetermined breaking connections are provided at the distal end of the individual wires, care is taken that, at these predetermining breaking points, the individual wires can detach in a defined manner at their distal end from the connection point, so that the functional wire mesh formed by the individual wires can open at its distal end. When the instrument is used, for example, as a calculus collecting instrument, this permits a distal releasing of an already collected calculus in the event of an overload, whereby it is avoided that the instrument tears at a different point and parts of the instrument possibly remain in the tissue and/or an excessively large collected calculus can no longer be released. Since the shaft section is formed by the converged individual wires themselves, it can be implemented with a comparatively small cross-section, which essentially corresponds to the sum of the individual wire cross-sections.

According to one aspect of the invention, the individual wires are mutually twisted in the entire shaft section and therefore distally to the transition into the basket-forming functional section. This provides a highly loadable shaft section while the cross-section is comparatively small without the use of additional devices, such as guiding or fixing sleeves or the like.

According to another aspect of the invention, the individual wires are mutually twisted in a distal end region proximally adjoining the predetermined breaking connections such that they rest against one another along this mutual twisting. This measure may be provided in addition or as an alternative to the measure of the twisting in the shaft section that continues distally to directly to the basket-forming functional section and provides an increased loading capacity of the predetermined breaking connection of the distal individual wire ends.

As an advantageous further development of the invention, the individual wires in the basket-forming functional section are untwisted, so that they form a corresponding wire basket there in a mutually untwisted manner in basket wire sections extending in pertaining longitudinal planes.

As a further development of the invention, the distal terminating body has a hemispherical or spherical terminating element, whereby the distal end of the instrument is provided with desired atraumatic properties.

As a further development of the invention, the distal terminating body has a terminating element for fixing the distal individual wire ends as well as a protective sleeve proximally adjoining the terminating element. In the protective sleeve, the individual wires are held with their distal end region. The protective sleeve may have the purpose of providing the respective predetermined breaking connection of the distal individual wire ends with a desired stability, for example, with respect to the bending open of the individual wires into a basket-forming functional condition.

In a further development of the invention, the distally end-side twisting of the individual wires is equal to that in the shaft section; that is, it has essentially the same twisting parameters, particularly an essentially equally large lead of the screw-shaped twisting turns.

In a further development of the invention, the individual wires are fixed with their proximal end directly to one another or to a proximal terminating body and/or, in the proximal end region, are received in a tubular gripping element. This implements advantageous designs of the multi-wire instrument in its proximal end section.

For the individual wires, for example, monofil wire material or stranded wire material can be used.

Other objects, advantages and novel features of the present invention will become apparent from the following detailed description when considered in conjunction with the accompanying drawings.

DETAILED DESCRIPTION OF THE DRAWINGS

In the following, advantageous embodiments will be explained in detail with reference to the drawings, in which, for an easier understanding, identical or functionally equivalent elements are marked with the same reference symbols. The calculus collecting instrument illustrated in FIG. 1 has a construction that is conventional per se, having a distal functional region 1 and a shaft region adjoining the latter proximally, which shaft region 2 is traversed by a grip connection tube at its rearward end and forms a so-called pull tube section 4. The core component of such calculus collecting basket instruments, as used, for example, for the endoscopic removal of gall or kidney stones, is a multi-wire instrument as shown in FIG. 3 in an implementation according to the invention.

Figure 3:
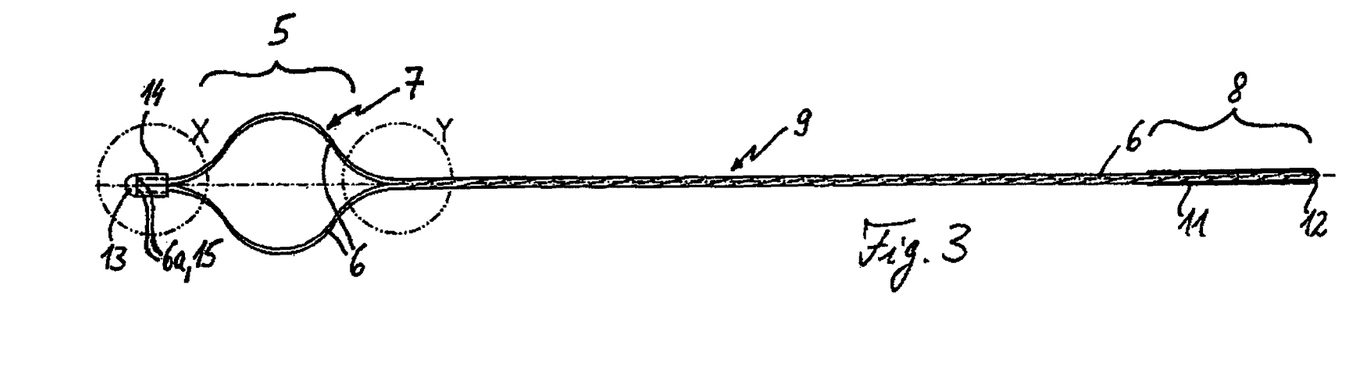
FIG. 3 is a lateral view of a multi-wire instrument usable for the calculus collecting basket instrument of FIG. 1.

As illustrated in FIG. 3, the multi-wire instrument contains a distal functional section 5, in which several individual wires 6 (here, in the illustrated example, two individual wires) in the illustrated functional condition, form a basket-forming functional wire mesh in the shape of a basket unit or loop unit 7 suitable for collecting calculi. At their distal end, the individual wires are combined and connected with one another. Proximally, the individual wires 6 are mutually twisted adjoining the functional section 5 and extend in this manner in one piece to a proximal end region 8 of the multi-wire instrument. Together with their twisted region, they form the entire corresponding shaft section 9 of the multi-wire instrument from the proximal end directly to the transition into the basket-forming functional section 5.

Figure 1:
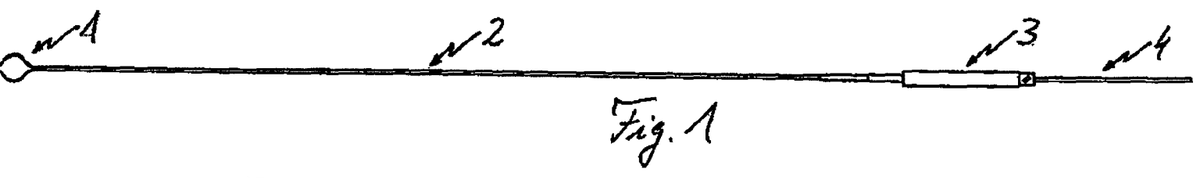
FIG. 1 is a schematic lateral view of an endoscopic calculus collecting instrument with the handle removed.
Figure 2:
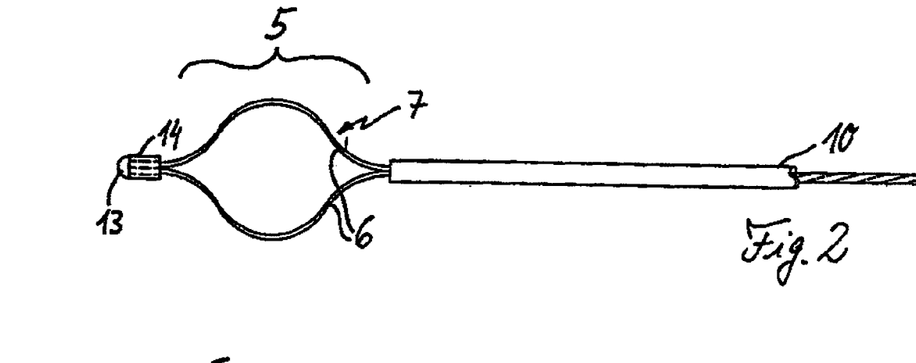
FIG. 2 is a detailed lateral view of a forward part of the calculus collecting basket instrument of FIG. 1.

In a manner known per se, when the multi-wire instrument is used in the calculus collecting basket instrument according to FIG. 1, it is guided with its shaft section 9 in an axially movable manner in a flexible guiding tube or guiding hose 10, as illustrated in greater detail in FIG. 2 for a forward part of the calculus collecting basket instrument of FIG. 1. As illustrated in FIG. 1, the grip connection tube 3 is coupled to the rearward end of the guiding tube 10. In a conventional manner, a handle, which is not shown, for operating the calculus collecting basket instrument can be connected to the grip connection tube 3.

In FIG. 2, the multi-wire instrument is in a condition in which it is moved out of the guiding tube 10 toward the front, and in which the distal functional section 5 is released from the guiding tube 10, and therefore the individual wires 6 can take up their basket-forming or loop-forming functional condition 7 there. From this condition, the multi-wire instrument can be moved axially into a pulled-in condition in which the guiding tube 10 receives the distal functional section 5 of the multi-wire instrument by means of it distal region, in which case the individual wires correspondingly fold together. From this pulled-in folded-together condition, the multi-wire instrument can then be moved out again toward the front in the distal functional section 5 while the individual wires 6 are unfolded in a basket-forming or loop-forming manner.

Figure 4:
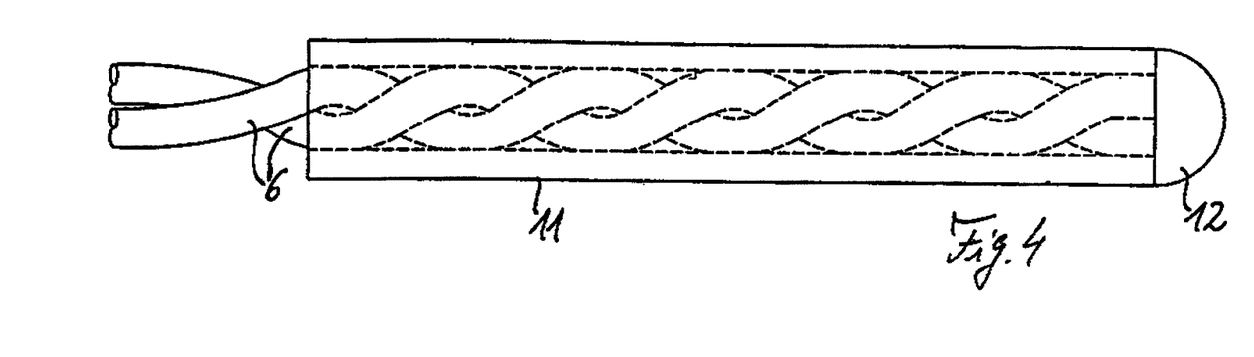
FIG. 4 is a detailed lateral view of a rearward end region of the multi-wire instrument of FIG. 3.

In the proximal end region 8, the shaft section 9 of the multi-wire instrument of FIG. 3 formed of the twisted individual wires 6 is received in a gripping sleeve 11 and is closed off flush on the face side by means of a hemispherical terminating element 12, as shown more clearly in the detailed view of FIG. 4. In an embodiment illustrated in FIG. 5, the twisted individual wires 6 are closed off at their proximal end without a receiving gripping sleeve by way of a hemispherical terminating element 12a.

As indicated in the above explanations, the finished calculus collecting instrument of FIG. 1 therefore consists of the multi-wire instrument of FIG. 3 as well as of the guiding tube 10 in addition to the coupled grip connection tube 3 and the handle (not shown) coupled thereto, in which case the shaft section 9 of the multi-wire instrument extends through the guiding tube 10 and the grip connection tube 3 and, with its proximal end region 8, forms the pull tube section 4 of the calculus collecting instrument.

Figure 6:
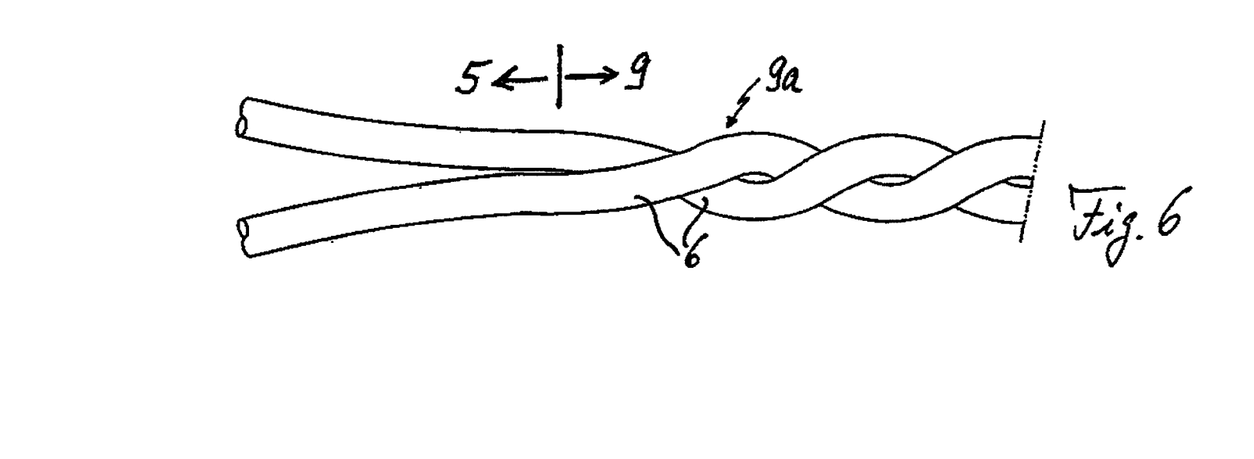
FIG. 6 is a detailed lateral view of a region Y of the multi-wire instrument of FIG. 3.

FIG. 6 is a detailed view of the transition (area Y of FIG. 3) of the individual wires 6 from their basket-forming or loop-forming bent-open untwisted functional condition in the distal functional section 5 directly to the proximally adjoining twisted distal end region 9a of the shaft section 9.

Figure 7:
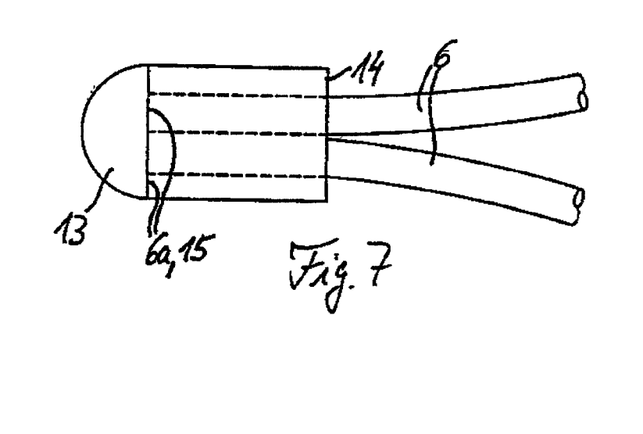
FIG. 7 is a detailed lateral view of a forward end region X of the multi-wire instrument of FIG. 3 with a hemispherical terminating element and a protective sleeve.

FIG. 7 is a more detailed view of the distal end region X of the multi-wire instrument of FIG. 3. As illustrated, the individual wires 6 are fixed with the distal ends 6a in an abutting manner to a hemispherical distal terminating element 13. These connections each are designed as a predetermined breaking connection 15; that is, the stability of these connections is set at a predefinable maximal value. When, during use, the loading of the predetermined breaking connections 15 of the distal individual wire ends 6a with the distal terminating element 13 exceeds this maximal value, this connection 15 will tear in a desired manner so that one or more of the individual wires 6 with their distal ends become detached, and the functional wire mesh 7 formed by the individual wires opens distally. In this manner, a collected calculus can be released again without any problem when it is found that it cannot be moved out through the calculus collecting instrument or crushed during a normal loading.

Furthermore, a protective sleeve 14 surrounding the individual wires 6 in their distal end region is fixed flush with the outside on the distal terminating element 13. By way of this protective sleeve 14, the predetermined breaking connection of the distal individual wire ends 6a on the distal terminating element 13 can be protected mainly against overloads resulting from a radial bending apart of the individual wires 6 in their distal functional section, so that an undesirable premature breaking of these predetermined breaking connections 15 because of such load effects is avoided.

Figure 8:
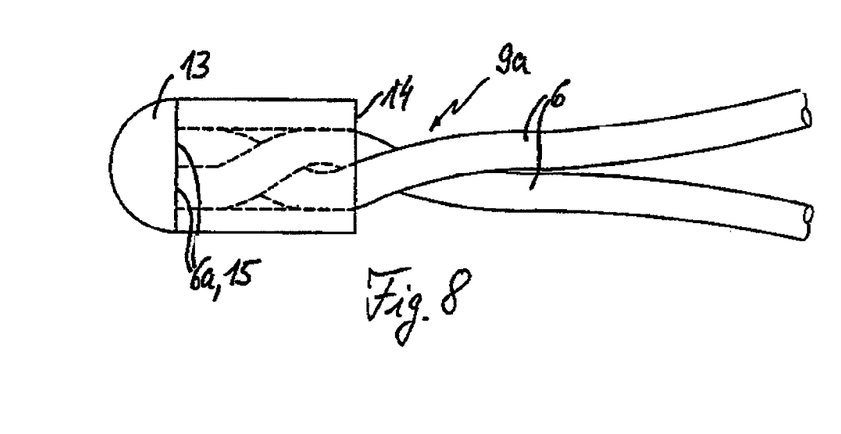
FIG. 8 is a view corresponding to FIG. 7 for an embodiment with an additional twisting of the individual wires in the distal end region.

FIG. 8 shows a very advantageous variation of the example of FIG. 7 with respect to the distal end region design. While, in the example of FIG. 7, the individual wires 6 in the distal end region are combined without any twisting and are guided in the protective sleeve 14 to the distal terminating element 13, in the example of FIG. 8, the individual wires 6 are combined from their distal functional section 5 toward the front while being twisted and are guided in the protective sleeve 14 to the distal terminating element 13. According to the conventional meaning of the term used herein, the distal twisting of the individual wires 6 means that the individual wires continuously rest against one another while winding around one another along this twisting region. This offers an additional protection against loading for the predetermined breaking connection 15 of the distal individual wire ends 6a at the distal terminating element 13. Preferably, the distal twisting of the individual wires 6 is implemented in the same manner as the proximal twisting of the individual wires 6 in the shaft section 9. The term "in the same manner" means that the one or more screw-type windings are implemented with essentially the same winding parameters for the two twistings, particularly as far as the lead and the outside diameter of the windings are concerned. In this case, the distal twisting can be implemented in the same direction or, as an alternative, in the opposite direction of the twisting in the shaft section 9.

Figure 9:
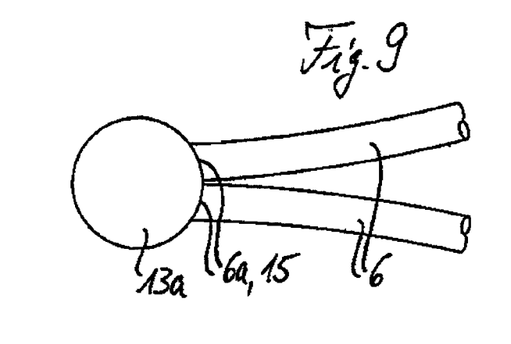
FIG. 9 is a view corresponding to FIG. 7 for an embodiment without a protective sleeve and with a spherical terminating element.

FIG. 9 shows another variation of the design of the distal end region X of the multi-wire instrument of FIG. 3 (or of any other multi-wire instrument according to the invention). In this variation, the individual wires 6 are guided untwisted and without a distal protective sleeve to a spherical distal terminating element 13a and are fixed to the latter with their distal ends 6a while forming the respective predetermined breaking connection 15.

Figure 10:
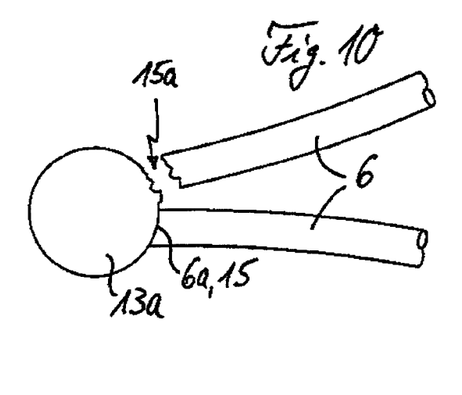
FIG. 10 is the view of FIG. 9 with a broken predetermined breaking connection of one of the individual wires.

FIG. 10 shows the view of FIG. 9 for a situation in which one of the individual wires 6 has become detached in the desired manner from the distal terminating element 13a at its predetermined breaking connection 15 because of an overload. As a result of the torn connection 15a, the detached individual wire and thereby the basket/loop unit as a whole formed by the two individual wires in this example can open distally in order to thereby, for example, release an already collected calculus. Such an overload case can, for example, be caused intentionally when it is found that a collected calculus cannot be moved out or crushed and therefore should be released by the calculus collecting basket instrument so that the latter can be pulled out of a tissue canal again without the calculus.

Figure 11:
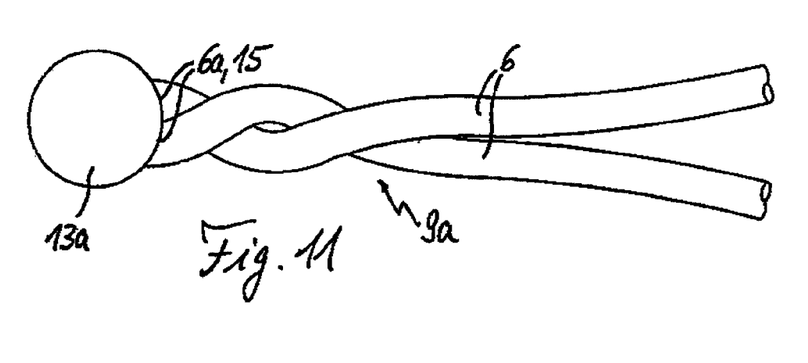
FIG. 11 is view corresponding to FIG. 9 for an embodiment with an additional twisting of the individual wires in the distal end region.

FIG. 11 shows a variation of FIG. 9, in which the individual wires 6 guided together from the distal functional section are twisted in their distal end region to the fixing of their distal ends 6a as a result of the predetermined breaking connections 15 at the spherical terminating element 13a. As in the example of FIG. 8, this increases the stability of the predetermined breaking connections 15, particularly with respect to a bending-open of the individual wires 6 in their basket/loop forming distal functional section.

Figure 12:
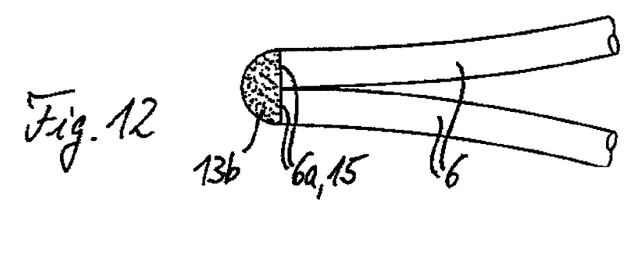
FIG. 12 is a view corresponding to FIG. 9 for an embodiment with a hemispherical terminating element.

FIG. 12 illustrates another variation of the design of the distal end region of the multi-wire instrument according to the invention again for a case of two individual wires 6 corresponding to the multi-wire instrument of FIG. 3. In this variation, the individual wires 6 are guided together from their distal functional section toward the front for the flush fixing of their distal ends 6a by means of the respective predetermined breaking connection 15 to a hemispherical terminating element 13b.

Figure 5:
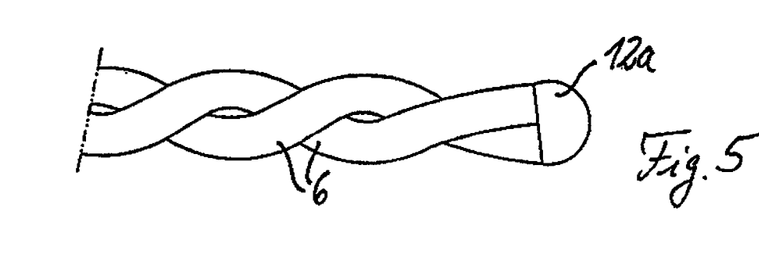
FIG. 5 is a lateral view of a rearward end region of a modified multi-wire instrument.
Figure 13:
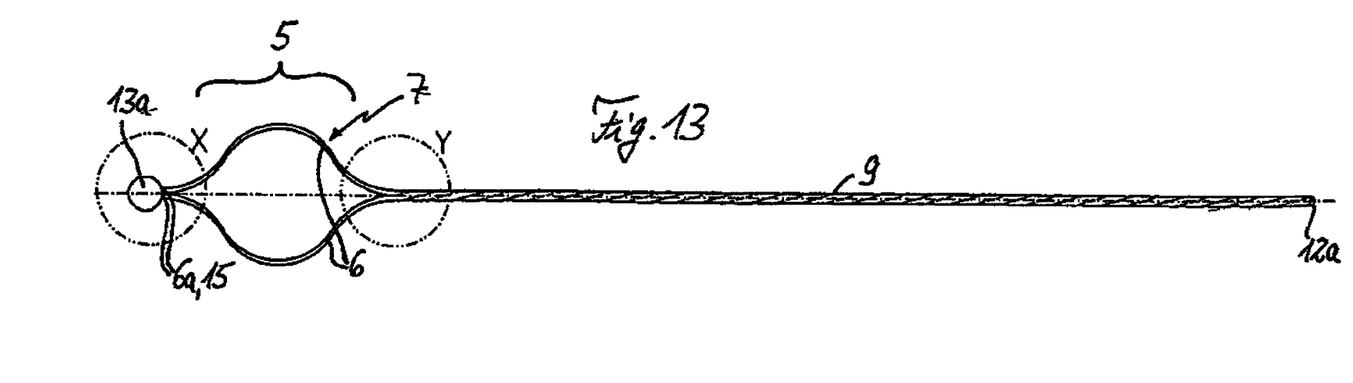
FIG. 13 is a lateral view of an embodiment of the multi-wire instrument of FIG. 3 with the proximal end region corresponding to FIG. 5 and the distal end region corresponding to FIG. 9.

In a view corresponding to FIG. 3, FIG. 13 shows an embodiment of the multi-wire instrument in which the individual wires twisted in the shaft region 9, in their proximal end region corresponding to FIG. 5, are closed off by the proximal terminating element 12a and, in their distal end region adjoining the distal functional section 5 corresponding to FIG. 9, are guided untwisted to the spherical distal terminating element 13a and are fixed to the latter by way of the predetermined breaking connections 15 with their distal ends 6a. As an alternative, the individual wires distally also end with a twisting analogous to the embodiment of FIG. 11.

Figure 14:
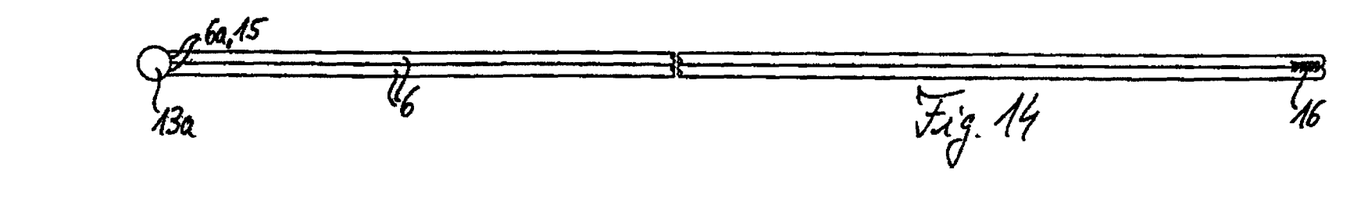
FIG. 14 is a lateral view of a blank condition of the multi-wire instrument of FIG. 13 in an initial manufacturing stage.

The multi-wire instrument according to the invention can be produced relatively easily, as illustrated in the following by the example of the multi-wire instrument of FIG. 13. FIG. 14 shows the multi-wire instrument of FIG. 13 in an initial manufacturing stage. As illustrated, first the individual wires 6 at their proximal end 6a are fixed by the predetermined breaking connections 15 to the spherical distal terminating element 13 and, as illustrated, in their proximal end region, are attached to one another and/or with their proximal face ends are attached to a proximal terminating element by way of a welded connection 16. Subsequently, the individual wires are then bent in the distal functional section into their desired configuration in order to form the required functional wire mesh and are twisted as desired in the proximally adjoining shaft section.

Figure 15:
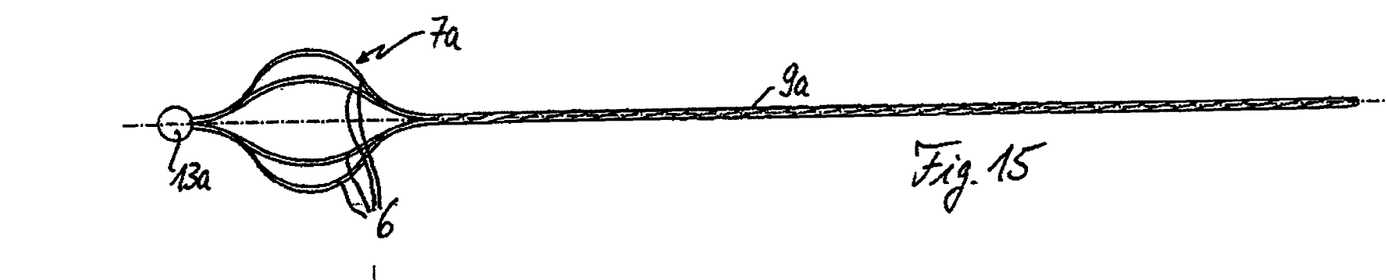
FIG. 15 is a lateral view corresponding to FIG. 13 for an embodiment with four, instead of two, individual wires.

FIG. 15 shows a variation of FIG. 13 in which the multi-wire instrument is formed of four individual wires 6 instead of two individual wires; that is, in the distal functional section, a wire basket 7a is formed in the functional condition from the four individual wires 6 bent open at an angular distance of 90° instead of the basket/loop unit formed in the example of FIG. 13 of two individual wires, and the shaft section 9a consists of four twisted individual wires.

Figure 16:
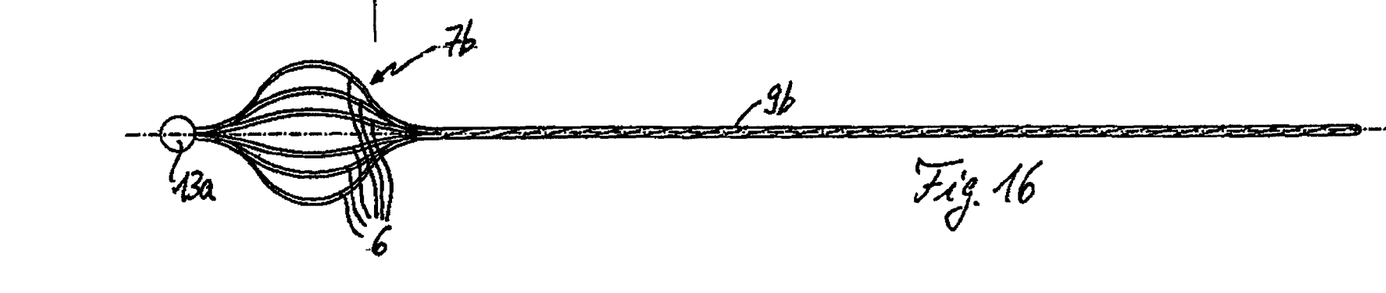
FIG. 16 is a lateral view corresponding to FIG. 13 for an embodiment with six, instead of four, individual wires.

FIG. 16 shows another variation of FIG. 3, in which the multi-wire instrument is constructed of six individual wires 6 which, in the distal functional section, when they are in the functional condition, are bent open at an angular distance of 60° to a corresponding basket unit 7b and, in the shaft section 9b, are continued in one piece to the proximal end of the multi-wire instrument while being twisted. In the distal end region, they are guided untwisted or, as an alternative, also while being twisted, to the distal terminating unit 13a and are fixed there.

The illustrated and above-described embodiments demonstrate that the invention provides a multi-wire instrument that can be implemented with relatively small cross-sections and minimizes the risk that wire connections tear at undesirable points when loaded. A contributing factor is, on the one hand, that the multi-wire instrument is continuously formed of individual wires extending in one piece from the distal to the proximal end of the multi-wire instrument, which individual wires are mutually twisted and/or held on one another in a different manner in the shaft section, for example, by way of weld points, while, in the distal functional section in the functional condition, they form a required basket-forming functional wire mesh, for example, also as a loop unit or filter unit. On the other hand, the individual wires are guided together in front of the distal functional section at their distal end and are directly fixed to one another or fixed to a distal terminating body by use of a respective predetermined breaking connection which is designed for a defined maximal load. In the event of an overload, the individual wires tear in a desired manner, in which case they are preferably also twisted in their distal end regions between the basket-forming functional section and the respective predetermined breaking connections.

The multi-wire instrument according to the invention therefore has no additional longitudinal wire section, with which the individual wires would have to be connected, and therefore also no wire connection points between its distal and proximal ends, so that there is also no danger that corresponding connection points tear in an unintended manner. Superelastic materials, such as an NiTi alloy, such a Nitinol, can preferably be used for the individual wires, but also steel materials, etc., customary for such usage purposes. Depending on the requirement, each individual wire may consist of monofil wire material or stranded material. As a result of the structural change in the material, it is relatively easy to design the fixing of the distal individual wire ends on one another or on a distal terminating body, as desired, as a predetermined breaking connection. Compared to multi-wire instruments, in the case of which the individual wires for the distal functional section are cut out of a pipe piece which, in the adjoining proximal region, functions as a shaft section, in the case of the multi-wire instrument according to the invention, smaller cross-sections or diameters can also be achieved in the shaft section and thus an increased rigidity can be achieved while the nominal diameter is the same. Thus, it is found that multi-wire instruments according to the invention, which can be used in calculus collecting basket instruments, can easily be produced with outside shaft diameters of less than 2.0 mm as a result of the twisting of the continuous individual wires and carry out the required functions, the total length of the multi-wire instrument for endoscopic applications typically being in the range of approximately one meter to several meters.

It is understood that the invention is not limited to endoscopic applications but can be used in all medical and other fields, in which multi-wire instruments are used which have a functional wire mesh of individual wires.

The invention claimed is:

1. A multi-wire instrument, comprising:
   a distal functional section in which several individual wires form small wire baskets, the individual wires being guided together at a distal end and connected with one another, the wires being fixed directly to one another or to a distal terminating body while forming a respective predetermined breaking connection;
   a shaft section extending between the distal functional section and a proximal end region of the multi-wire instrument;
   wherein the individual wires extend in one piece from their distal end to the proximal end region of the multi-wire instrument, and the shaft section is formed by the individual wires combined there and held together;
   wherein the individual wires are mutually twisted in the entire shaft section to a basket-forming functional section, changing from the twisted distal end of the shaft section while radially expanding to the basket-forming functional section; and wherein the individual wires are twisted in a distal end region distally adjoining the basket-forming functional section and rest against one another along this twisting.

2. The multi-wire instrument according to claim 1, wherein the individual wires are untwisted in the basket-forming functional section.

3. The multi-wire instrument according to claim 1, wherein the distal terminating body contains a hemispherical or spherical terminating element.

4. The multi-wire instrument according to claim 2, wherein the distal terminating body contains a hemispherical or spherical terminating element.

5. The multi-wire instrument according to claim 1, wherein the distal terminating body contains a terminating element, to which the distal individual wire ends are fixed, and a protective sleeve proximally adjoining the terminating element and holding the distal end region of the individual wires.

6. The multi-wire instrument according to claim 2, wherein the distal terminating body contains a terminating element, to which the distal individual wire ends are fixed, and a protective sleeve proximally adjoining the terminating element and holding the distal end region of the individual wires.

7. The multi-wire instrument according to claim 1, wherein the twisting of the individual wires in the distal end region takes place in the same manner and is neither in a same direction or in an opposite direction to their twisting in the shaft section.

8. The multi-wire instrument according to claim 2, wherein the twisting of the individual wires in the distal end region takes place in the same manner and is neither in a same direction or in an opposite direction to their twisting in the shaft section.

9. The multi-wire instrument according to claim 3, wherein the twisting of the individual wires in the distal end region takes place in the same manner and is neither in a same direction or in an opposite direction to their twisting in the shaft section.

10. The multi-wire instrument according to claim 5, wherein the twisting of the individual wires in the distal end region takes place in the same manner and is neither in a same direction or in an opposite direction to their twisting in the shaft section.

11. The multi-wire instrument according to claim 1, wherein the individual wires are at least one of:
    (a) fixed with their proximal end directly to one another or to a proximal terminating body, and
    (b) in the proximal end region, received in a grip tube element.

12. The multi-wire instrument according to claim 2, wherein the individual wires are at least one of:
    (a) fixed with their proximal end directly to one another or to a proximal terminating body, and
    (b) in the proximal end region, received in a grip tube element.

13. The multi-wire instrument according to claim 3, wherein the individual wires are at least one of:
    (a) fixed with their proximal end directly to one another or to a proximal terminating body, and
    (b) in the proximal end region, received in a grip tube element.

14. The multi-wire instrument according to claim 5, wherein the individual wires are at least one of:
    (a) fixed with their proximal end directly to one another or to a proximal terminating body, and
    (b) in the proximal end region, received in a grip tube element.

15. The multi-wire instrument according to claim 7, wherein the individual wires are at least one of:
    (a) fixed with their proximal end directly to one another or to a proximal terminating body, and
    (b) in the proximal end region, received in a grip tube element.

16. The multi-wire instrument according to claim 1, wherein the respective individual wire comprises one of a monofil wire material and a stranded wire material.

17. The multi-wire instrument according to claim 1, wherein the instrument is an endoscope.

* * * * *